United States Patent [19]

Valdespino et al.

[11] Patent Number: 4,553,552
[45] Date of Patent: Nov. 19, 1985

[54] HEMODIALYSIS METER

[76] Inventors: Joseph M. Valdespino, 5023 Golf Club Pkwy., Orlando, Fla. 32808; Allen K. Holcomb, 200 W. Gore St., Orlando, Fla. 32806; William M. Hobby, 244 Sylvan Blvd., Winter Park, Fla. 32789

[21] Appl. No.: 581,996

[22] Filed: Feb. 21, 1984

[51] Int. Cl.[4] .............................................. A61B 5/00
[52] U.S. Cl. .................................... 128/637; 128/765; 128/771
[58] Field of Search ............... 128/637, 635, 765, 771, 128/DIG. 1, 13, 734, 763, 770; 604/38, 404, 62 R; 324/71.1, 71.4, 450, 446, 448; 73/26, 54, 336.5, 863.83, DIG. 8; 422/68, 73, 79; 436/68

[56] References Cited

U.S. PATENT DOCUMENTS 3,674,012  7/1972  Sage ..................................... 128/637
4,083,363  4/1978  Philpot, Jr. .......................... 128/637
4,388,043  6/1983  Preiss .................................... 324/448

Primary Examiner—Lee S. Cohen
Assistant Examiner—Steven Falk
Attorney, Agent, or Firm—William M. Hobby, III

[57] ABSTRACT

A hemodialysis conductivity meter apparatus is provided for measuring dialysate concentration using a self contained syringe. The meter includes a syringe body having a needle attached thereto with a syringe plunger coacting with the body to draw fluid into the body. A pair of electrodes are positioned for contact with the fluid in the syringe body while a power source located on the syringe generates an electric current reading across the electrodes responsive to the fluid in the syringe body. An output meter attached to the syringe gives an immediate reading of the conductivity of the fluid. The plunger of the syringe may be used to keep the electrodes clean and an alternate embodiment allows the syringe plunger to switch the meter on when drawing fluid thereinto and to switch the meter off when removing the plunger or pushing the liquid out of the syringe body.

13 Claims, 5 Drawing Figures

U.S. Patent   Nov. 19, 1985   4,553,552
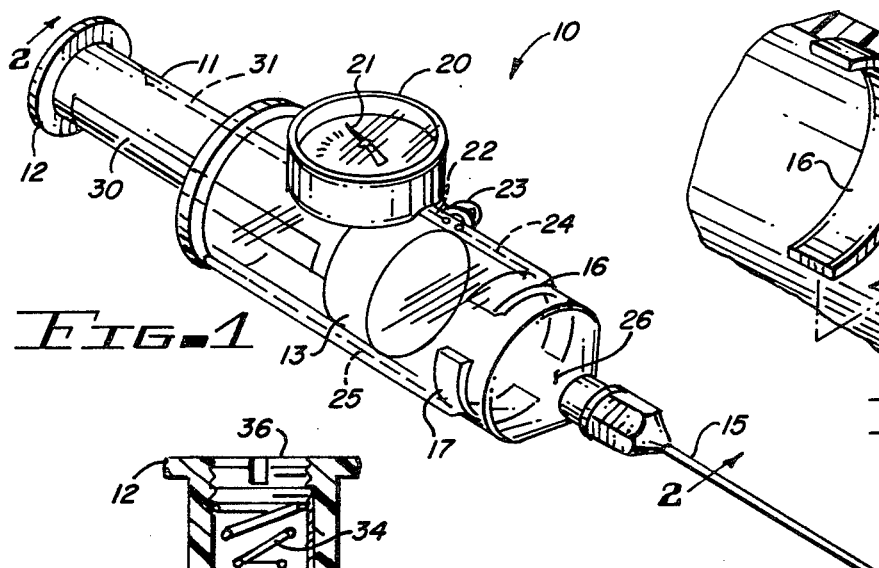
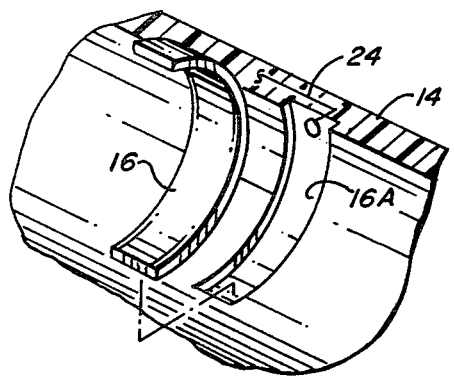
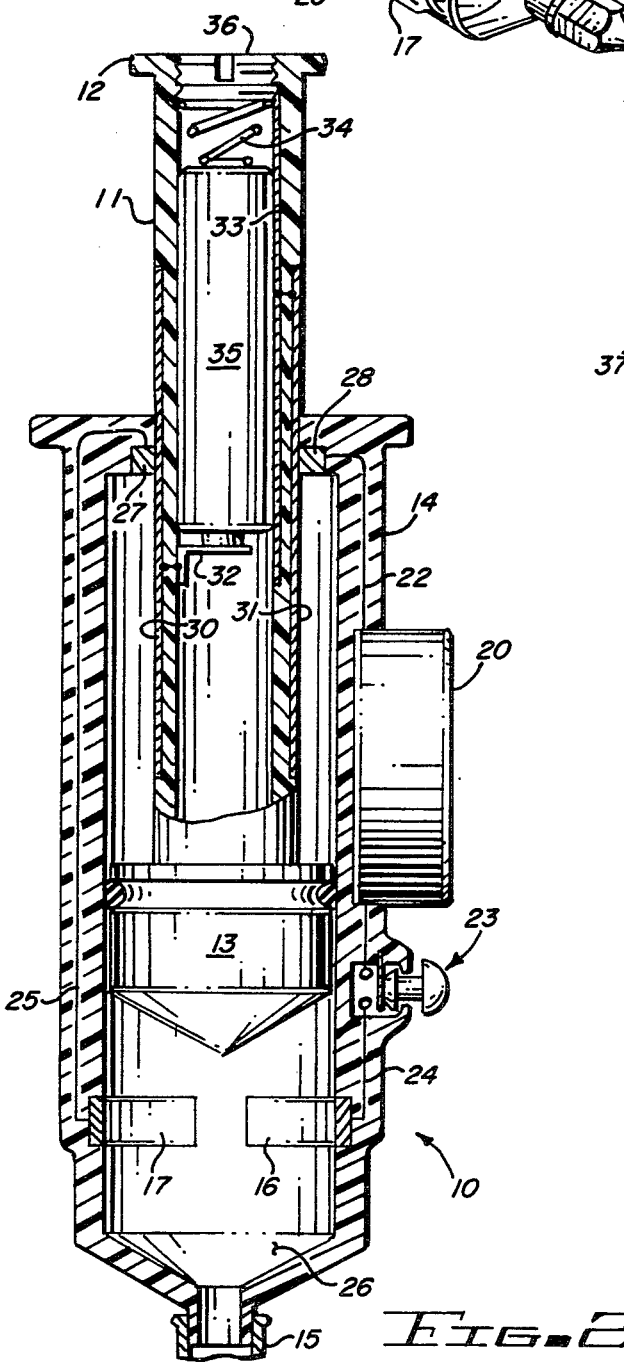
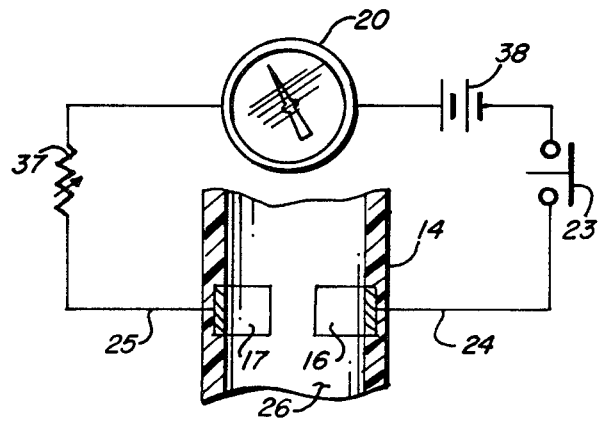
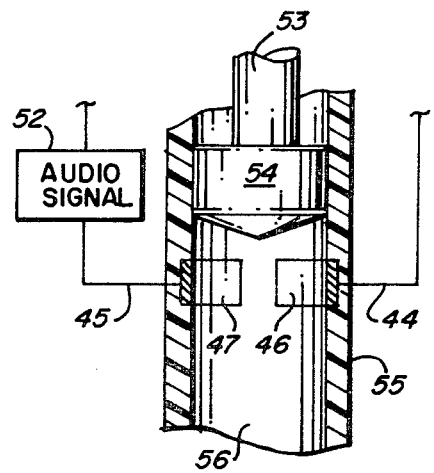

HEMODIALYSIS METER

BACKGROUND OF THE INVENTION

The present invention relates to a dialysate meter for measuring the conductivity in a hemodialysis bath.

In the past, it has been common to monitor the dialysate in a hemodialysis bath to ascertain that the electrolyte solution has not become diluted or more concentrated than desired to maintain the proper operating conditions for dialysis since the dialysate is an electrolyte solution, it can be monitored with direct conductivity measured between predetermined electrodes at a predetermined spacing in the electrolyte solution. This has commonly been done in the past by removing a small amount of dialysate solution and placing it into a special container and then taking the container to a different position in a laboratory and measuring the conductivity of the solution. This requires an electrical circuit to compensate for temperature differentials because the dialysate solution is being placed in a different container in a room with different temperature and being moved to a different position. The present invention is directed to a simplified dialysate meter which takes an instantaneous reading of the solution being withdrawn from the hemodialysis bath, so that it is unnecessary to make adjustments for temperature variation between the solution being measured and the temperature of the hemodialysis bath. This allows a reliable low cost meter to be produced for additional monitoring of the electolyte solution in the hemodialysis bath in a portable meter.

SUMMARY OF THE INVENTION

The present invention relates to a dialysate meter in which a syringe body having a needle attached thereto is utilized in the measuring of the dialysate in a hemodialysis bath. A syringe plunger coacts with the syringe body to draw a fluid into the body when the plunger is slid in one direction in the body. A plurality of electrodes are mounted to the syringe body positioned for contact with the fluid drawn into the syringe body. A source of electric power, such as a small battery, is located on the syringe and will produce an electrical current in the meter when a potential is placed across the electrodes in the syringe body. A current signal output means, such as a galvanometer, generates a visual output responsive to the flow of electrical current between the electrodes. An audible signal may also be provided for the syringe as well as a switch. An alternate embodiment has a plunger automatically actuates the meter upon drawing the liquid into the syringe body and shuts off the meter when the liquid is expelled from the syringe body or the plunger is removed from the body.

BRIEF DESCRIPTION OF THE DRAWINGS

Other objects, features and advantages of the present invention will be apparent from the written description and the drawings in which:

FIG. 1 is a perspective view of a dialysate meter in accordance with the present invention;

FIG. 2 is a side sectional view of the meter of FIG. 1;

FIG. 3 is a partial exploded perspective view of an electrode in the syringe;

FIG. 4 is a partial schematic of an electrical circuit for use in accordance with the syringe meter of FIG. 1; and FIG. 5 is a partial sectional view of an alternate embodiment of the dialysate meter.

DESCRIPTION OF THE PREFERRED EMBODIMENT

Referring to the drawings and especially to FIGS. 1 and 2, a dialysate syringe meter 10 is shown having a syringe plunger 11 with a handle portion 12 and connected to a plunger piston 13 sliding in a syringe body 14. The syringe body 14 has a syringe needle 15 attached to the end thereof so that this portion of the invention acts in accordance with conventional medical syringes. However, the syringe body 14 has an arcuate anode electrode 16 mounted therein and an cathode electrode 17 mounted opposite the anode 16. Both electrodes are arcuate following the circular walls of the syringe body 14 so that the plunger piston 13 can pass thereby wiping electrodes off as it moves back and forth across the electrodes to thereby remove any accumulated salts with every passage of the plunger 13. The syringe body 14 and the syringe plunger 11 are normally made of polymer materials while the plunger 13 is typically made of a natural or synthetic elastomer. The syringe body 14 has a galvanometer 20 with a needle 21 mounted thereon. The galvanometer 20 may be fixedly attached to the body or may be removably attached thereto if desired. This type of meter can also, of course, be a digital meter without departing from the scope of the invention. The galvanometer has one of its leads 22 connected to a small battery 35, in a battery holder located in the plunger body 11 in this embodiment, even though it can be mounted in other places on the syringe as desired. A push button switch 23 may be used but is not necessary since the battery can be automatically disabled by movement of the plunger. The switch 23 is attached to the syringe body 14 and is connected to the conductor 24. The electrodes 16 and 17 are mounted in a syringe in a fixed, sealed or molded fashion to prevent any leakage therearound and are encased in the polymer body except for the lead 24 connected to the anode 16 and the lead 25 connected to the cathode electrode 17. The battery is used even though it is also contemplated that the use of dissimilar metals in the electrodes 16 and 17 will produce electrical current flow as an electrolytic cell when an electrolyte solution is in the inside chamber 26 of the syringe body 14 covering the electrodes. The galvanic cell has been shown to operate with the proper selection of dissimilar metal electrodes while doing away with the battery which must be replaced from time to time. However, a galvanic cell depends upon the electrodes being kept clean and can be difficult to obtain a sufficient degree of sensitivity to small changes in the electrolyte solution from the hemodialysis bath.

The hemodialysis bath dialysate solution conductivity is measured to determine the concentration of the electrolyte solution for proper operation of the dialysis machines. The plunger 11 may have the battery 35 placed therein through the threaded cap 36 having a spring 34. The battery negative terminal contacts the conductor 33 through the spring 34 and is connected to the conductor 31 along the outside of the plunger body 11. The battery positive terminal connects to the contact 32 and conductor surface 30 on the outside of the plunger 11 body. This allows the contact strip 31 to make contact with the contact 28 and with the meter 20 while conductor 30 connects to the contact 27 and conductor 25. This arrangement serves to provide a convenient positioning of the battery and will automatically disengage the battery when the plunger 11 is removed from the syringe body 14 or is pushed all the way into the syringe body 14 where the conductors 30 and 31 no longer are in contact with the contacts 27 and 28. This occurs when the test solution is expelled from the syringe. However, it will be clear that no current will be flow unless a solution is in the syringe covering the electrodes 16 and 17.

FIG. 4 shows an electrical diagram in accordance with the invention in which the galvanometer 20 has a battery 38 connected in the line 24 through a switch 23. The electrical conductor 24 is connected to the anode 16 while an electrical conductor 25 is connected to an Cathode 17 with each electrode forming an arcuate surface inside the syringe chamber 26. A variable resistor 37 is mounted in the circuit for nulling the galvanometer 12 for proper calibration of the meter.

The plunger piston 13 shown in FIGS. 2 and 5 is made of an elastomer, such as of natural rubber, which wipes the arcuate electrodes 16 and 17 along their surfaces to prevent the buildup of salts on the surface. FIG. 5 shows an alternate embodiment in which a syringe body 55 has a syringe plunger 53 therein with a plunger piston 54. The dialysate is drawn into the chamber 56 past the arcuate electrodes 46 and 47. The Electrodes 46 and 47 are connected through electrical conductors 44 and 45 through a variable resistor to a galvanometer as shown in FIG. 4. Switching is accomplished by the electrolyte solution covering the electrodes and then being expelled from the syringe. After a measurement has been taken, pushing the plunger back into the body 31 will remove the dialysate to save the battery. In contrast, the embodiment of FIG. 1 requires the dialysate to be drawn through the needle into the chamber 26 and the electrical switches activated to get a meter reading but avoids a reading until ready and avoids any waste of battery power. The advantage of the present invention is that it eliminates more complex electrical circuitry found in similar devices which require corrections for temperature variations when the dialysate is removed to a different location and while providing is a portable self contained unit that allows a needle to be inserted into a sealed closed system to prevent any contamination of solution by withdrawing a small amount of the solution and taking an instantaneous reading. It is, of course, to be understood that dialysis machines have a variety of monitoring systems either incorporated thereinto or used therewith for the safety of the patient.

It should be clear at this point that a dialysate meter has been provided for measuring the dialysate solution in a hemodialysis bath by measuring the conductivity of the electrolyte solution which is fully incorporated into a syringe without any electrical or other remote connections to the meter. It will also be clear that variations are comtemplated, such as an audible electrical signal generated by a buzzer 52, if the dialysate solution exceeds a certain predetermined value. The electric buzzer 52 takes only a small amount of current and would seldom be activated. The dialysate meter can also have incorporated a low battery warning signal even though the galvanometer 12 and electrical buzzer 43 will also give a warning that the battery needs to be checked. Finally, it is contemplated that a temperature sensor can be included in the syringe for taking temperature reading of the solution at the same time as measuring the conductivity. Accordingly, the present invention is not to be considered as limited to the forms shown which are to be considered illustrative rather than restrictive.

We claim:

1. A conductivity meter comprising in combination:
   a syringe body having a needle attached thereto;
   a syringe plunger coacting with the syringe body to draw a fluid into said body when slid in one direction in said body;
   a plurality of electrodes attached to said syringe body positioned for contact with a fluid in the syringe body;
   a source of electrical power located on said syringe body and being operatively connected to at least one of said electrodes; and
   signal output means for generating a visual output responsive to the conductivity of an electrolyte solution covering said electrodes when said source of electrical power is applied across the electrodes, whereby a self-contained syringe can test a liquid by drawing a portion of fluid into the syringe.

2. A conductivity meter in accordance with claim 1 in which said plurality of electrodes includes a pair of arcuate electrodes mounted in the walls of said syringe body.

3. A conductivity meter in accordance with claim 2 in which said syringe plunger has means to wipe across the electrodes when drawing liquid into said syringe body or expelling liquid from said syringe body.

4. A conductivity meter in accordance with claim 3 in which said source of electrical power is a battery having a switch means connected thereto which is actuated for taking a reading on said signal output means.

5. A conductivity meter in accordance with claim 4 including a variable resistor means attached to said syringe body for calibrating said signal output means.

6. A conductivity meter in accordance with claim 1 in which said syringe body has switching means for switching the signal output means on and off.

7. A conductivity meter in accordance with claim 6 in which the source of power is a battery mounted in said syringe plunger and said switching means includes a pair of electrical contacts mounted on said syringe plunger body and said syringe body has a pair of electrical contacts mounted thereon electrically coupled to said syringe plunger electrical contacts whereby contact between said syringe plunger contacts and said syringe body contacts can be disengaged by movement of said syringe plunger until the contacts disengage.

8. A conductivity meter in accordance with claim 7 in which said plunger has a threaded cap thereinto.

9. A conductivity meter in accordance with claim 1 in which said signal output means includes an electrically actuated means for generating an audible signal responsive to the conductivity of the electrolyte solution.

10. A syringe meter for testing fluids drawn into the syringe comprising in combination:
    a syringe body having a needle attached thereto;
    a syringe plunger having a piston on the end thereof coacting with said syringe body to draw a fluid into said body when slid in one direction in said body;
    a pair of electrodes attached to said syringe body inside said syringe body for contact with a fluid drawn thereinto;
    a visual meter attached to said syringe body and operatively coupled to said electrodes for producing a visual output from the signal generated by said electrodes; and a power source attached to said body and operatively coupled to said visual meter and electrodes for operation of said meter attached to the syringe body, whereby the syringe can be used to take measurements from the electrodes incorporated in the syringe.

11. A syringe meter in accordance with claim 10 in which said syringe plunger has means thereon to actuate said meter upon movement of said plunger in said syringe body.

12. A syringe meter in accordance with claim 11 in which said syringe plunger piston has means to wipe said electrodes when pushed thereby in said syringe body.

13. A syringe meter in accordance with claim 12 in which said electrodes are arcuate shaped metal electrodes formed in the walls of said syringe body.

* * * * *